United States Patent [19]

Kaneko et al.

[11] 4,108,764
[45] Aug. 22, 1978

[54] METHOD AND APPARATUS FOR REMOVING GAS FROM INTERIOR OF HOLLOW-FIBER PERMEABILITY APPARATUS

[75] Inventors: Noriaki Kaneko; Yasushi Joh, both of Yokohama, Japan

[73] Assignee: Nippon Ceon Co., Ltd., Tokyo

[21] Appl. No.: 797,765

[22] Filed: May 17, 1977

[30] Foreign Application Priority Data

May 20, 1976 [JP] Japan .................................. 51-58299

[51] Int. Cl.² ............................................ B01D 13/00
[52] U.S. Cl. ................................ 210/22 A; 210/23 F; 210/23 H; 210/321 A; 55/158; 210/199; 210/206
[58] Field of Search .................. 55/158; 210/199, 206, 210/22, 23 H, 321 B, 321 R, 436

[56] References Cited

U.S. PATENT DOCUMENTS

| | | | |
|---|---|---|---|
| 3,228,876 | 1/1966 | Mahon | 210/22 |
| 3,384,242 | 5/1968 | Kudlaty et al. | 210/436 |
| 3,536,611 | 10/1970 | DeFilippi et al. | 210/22 |
| 3,691,068 | 9/1972 | Cross | 210/22 |
| 3,795,088 | 3/1974 | Esmond | 210/436 X |
| 3,827,561 | 8/1974 | Serfags et al. | 210/436 |
| 3,939,078 | 2/1976 | Servas et al. | 210/436 |

*Primary Examiner*—Charles N. Hart
*Assistant Examiner*—E. Rollins Cross
*Attorney, Agent, or Firm*—McDougall, Hersh & Scott

[57] ABSTRACT

In a method and apparatus for removing gas from the interior of a hollow-fiber permeability apparatus in which a permeating region of a housing contains a bundle of hollow fibers, and materials can selectively permeate through the membranes formed by the permeable walls of the hollow fibers, between first and second fluids flowing through the housing inside and outside the fibers respectively, at least one of first and second materials to produce carbonic acid gas by mutual chemical reaction is contained in a flow path for the first fluid and/or another flow path for the second fluid, and the first and second materials react with each other in at least one part of the apparatus to produce carbonic acid gas, whereby the gas previously existing in the interior of the housing is substituted with the produced carbonic acid gas.

55 Claims, 2 Drawing Figures

METHOD AND APPARATUS FOR REMOVING GAS FROM INTERIOR OF HOLLOW-FIBER PERMEABILITY APPARATUS

BACKGROUND OF THE INVENTION

1. Field of the Invention:

This invention relates to a method and apparatus for removing gas from the interior of a hollow-fiber permeability apparatus in which a permeating region of a housing contains a bundle of hollow fibers, and materials can selectively permeate through the membranes formed by the permeable walls of the hollow fibers, between first and second fluids flowing through the housing inside and outside the fibers respectively, and more particularly to a method and apparatus for removing gas from the interior of a hollow-fiber permeability blood dialysis apparatus of the dry type by which bubble removing operation before use for blood dialysis can be remarkably improved. These apparatuses are also known in the trade as hemodialyzers.

2. Description of the Prior Art:

Recently, blood dialysis apparatus for artificial kidneys, having permeable walls of, for example, cellulose, are widely used, greatly assisting patients suffering from renal failure.

As well known, blood dialysis is effected a few times per week for a patient suffering from chronic renal failure, so as to prolong the life of the patient or return the patient to the social life. In the present blood dialysis apparatus, permeable membranes of cellulose in the form of film or tube are piled, wound or bundled to obtain the total membrane area of about one square meter. The dialysate contacts with blood through the membranes.

The permeable membranes are dipped into water or impregnated with plasticizer such as glycerin in order to maintain a desired selective permeability of the permeable membranes, in the blood dialysis apparatus. In the blood dialysis apparatus of the wet type, the permeable membranes are dipped into water. And in the blood dialysis apparatus of the dry type, the permeable membranes are impregnated with plasticizer. A so-called "plate type" blood dialysis apparatus having piled permeable films, and a so-called "coil-type" blood dialysis apparatus having tubes wound into coil are generally of the dry type, and sterilized with ethylene oxide gas or with irradiation of γ-ray.

Recently, hollow-fiber permeability apparatus have become popular in which hollow fibers formed into capillary tubes having an inner diameter of several hundreds microns are used. The most remarkable advantages of the hollow fiber permeability apparatus are that it provides a relatively large effective surface area of membrane and that the blood priming volume can be smaller than the coil-type and plate-type blood dialysis apparatus. The hollow-fiber permeability apparatus can be smaller-sized, and is superior in withstanding pressure and in security. In the hollow-fiber permeability blood dialysis apparatus, the hollow fibers are dipped into formalin, or it is impregnated with plasticizer and sterilized with ethylene oxide gas. Thus, hollow-fiber permeability apparatus of both types are marketed.

Before the blood dialysis apparatus is used for blood dialysis, it is required that blood flow path be filled with physiological saline solution. Such an operation is called a "bubble-removing operation". When the blood dialysis is started in the condition that many air bubbles (fine air bubbles) remain in the blood dialysis apparatus and circuits connected to the blood dialysis apparatus, there is the risks that the air bubbles would enter into the blood vessel of the patient during dialysis, disturb a preferable flow from the view point of hydrodynamics, cause thrombus, and/or reduce the effective membrane area.

In the coil type blood dialysis apparatus, the tubes are pressed flat to purge air therefrom. Accordingly, when physiological salin solution is introduced into the blood dialysis apparatus, there is little problem in the air-bubble removing operation.

In the bubble removing operation of the plate-type blood dialysis apparatus, the apparatus is inclined or vertically placed, and physiological salin solution is introduced into the blood flow path from below the apparatus. Thus, the air bubbles can be easily removed.

In most of the marketed hollow-fiber permeability apparatus, the hollow fibers are dipped into formalin. Fine bubbles are previously removed from the interiors of the hollow fibers. It is relatively easy to remove little bubbles remaining in the interiors of the hollow fibers. However, it requires a long time to remove and wash formalin from the hollow fibers, and a simpler system is desired. Moreover, the apparatus containing the formalin is unduly heavy and inconvenient for handling.

Recently, hollow-fiber permeability apparatus of the dry type are marketed which overcome the disadvantage of the hollow fiber permeability apparatus containing formalin. However, it requires a long time and much labor to purge fine bubbles from the interiors of the hollow fibers when physiological saline solution is introduced into the apparatus before use for dialysis.

It has been proposed to utilize carbonic acid gas in order to perfectly fill the blood flow path with physiological salin solution. In that method, air bubbles are substituted with carbonic acid gas in the blood flow path. Carbonic acid gas has a high water-solubility, and so it is easily dissolved into physiological saline solution. Accordingly, the blood flow path is perfectly filled with physiological saline solution.

There are some problems with this system since, in practice, a liquefied carbonic acid gas container is brought into a dialysis room. Carbonic acid gas is blown into the dialysis apparatus. Such a procedure is laborous and the use of high pressure gas is not preferable from the viewpoint of security. Besides, sealed dialysis apparatus previously containing carbonic acid gas are proposed for market. Such a dialysis apparatus has the remarkable inevitable disadvantage that some carbonic acid gas leaks out from the apparatus and is substituted with air, before use.

SUMMARY OF THE INVENTION

An object of this invention is to provide a method and apparatus for removing gas from the interior of a hollow fiber permeability apparatus by which bubbles or gas can be substantially perfectly purged from the interior of the hollow-fiber permeability apparatus.

Another object of this invention is to provide a method and apparatus for removing gas from the interior of a hollow fiber permeability apparatus by which bubbles or gas can be very simply and securely removed.

A still another object of this invention is to provide a method and apparatus for removing gas from the interior of a hollow-fiber permeability apparatus, by which the apparatus can be marketed containing materials for removing gas, and thereby the apparatus can be very effective and economical.

In accordance with one aspect of this invention, a method for removing gas from the interior of a hollow-fiber permeability apparatus in which a permeating region of a housing contains a bundle of hollow fibers, and material can selectively permeate through the membranes formed by the permeable walls of the hollow fibers, between first and second fluids flowing through the housing inside and outside the fibers respectively, includes the steps of:

(A), reacting a first material with a second material in at least one part of the apparatus, to produce carbonic acid gas; and (B), substituting the gas previously existing in the interior of the housing with the produced carbonic acid gas.

In accordance with another aspect of this invention, in a hollow-fiber permeability apparatus in which a permeating region of a housing contains a bundle of hollow fibers, and materials can selectively permeate through the membranes formed by the permeable walls of the hollow fibers, between first and second fluids flowing through the housing inside and outside the fibers respectively, at least one of first and second materials to produce carbonic acid gas by mutual chemical reaction is contained in a flow path for the first fluid and/or another flow path for the second fluid, to remove gas from the interior of the hollow fiber permeability apparatus.

The other objects, features and advantages of this invention will be apparent from the following description taken in conjunction with the accompanying drawings.

DESCRIPTION OF THE PREFERRED EMBODIMENTS

Figure 1:
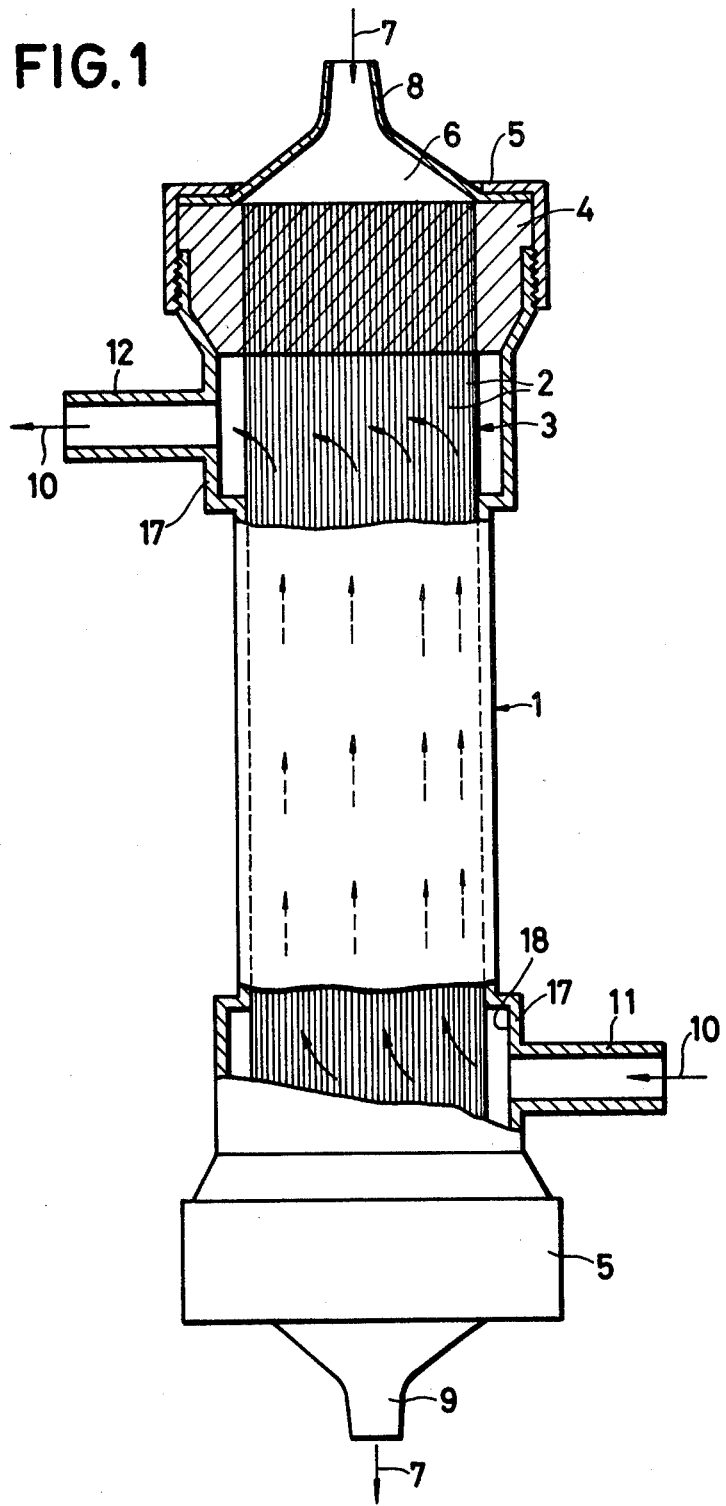
FIG. 1 is a front view of a blood dialysis apparatus for artificial kidneys, according to one embodiment of this invention, partly broken away.

According to this invention, carbonate and/or hydrogencarbonate is decomposed with acidic material in a short time, to produce carbonic acid gas.

For example, as carbonate and hydrogen carbonate which can be used, there are sodium carbonate, sodium hydrogen carbonate, sodium sesquicarbonate, ammonium carbonate, ammonium hydrogen carbonate, calcium carbonate, calcium hydrogen carbonate, magnesium carbonate, calcium magnesium carbonate, and mixtures of two or more of them. From the viewpoint of stability and intoxicity, sodium carbonate, sodium hydrogen carbonate, sodium sesquicarbonate, calcium carbonate and calcium hydrogen carbonate are preferable.

The acidic material may be inorganic or organic, and solid or liquid, so far as carbonate or hydrogen carbonate can be decomposed with the acidic material. For example, as inorganic acid for the acidic material, there are hydrochloric acid, sulfuric acid, nitric acid, phosphoric acid, pyraphosphoric acid, tripolyphosphoric acid, sulfurous acid, and mixtures of two or more of them.

Example of acidic organic comound having at least one of carboxyl group and sulfonic group, or its derivatives are formic acid, acetic acid, glycolic acid, glyceric acid, lactic acid, pyruvic acid, 2-chloropropionic acid, oxaloacetic acid, citric acid, oxalic acid, tartaric acid, fumaric acid, maleic acid, malonic acid, chlorobenzoic acid, phthalic acid, aconitic acid, salicylic acid, citramalic acid, gentisic acid, D-glucaric acid, gluconic acid, glutaric acid, gallic acid, L-gluconic acid, hydroxyphthalic acid, galacturonic acid, lactobionic acid, 2-nitro-4-sulfobenzoic acid, P-toluenesulfonic acid, benzene sulfonic acid, 4-hydroxyisophthalic acid and mixtures of two or more of them.

Amino acid such as glutamic acid and hydroxyglutamic acid, or inorganic acid salt of amino acid may be used as the acidic material. Example of inorganic acid salt of organic acid having basic nitrogen (for example, primary amine, secondary amine or tertiary amine) are hydrochloride of sulfate of or phosphate of aminosalicylate, cinchomeronate, cinchophene, indican, induleacetate, isonicotinate, isonipecotate, nicotinate, pipecolate, proline, and mixtures of two or more of them. From the viewpoint of practical use, lactic acid, pyruvic acid, glutamic acid and hydrochloride glutamate are preferable, since they are intoxic, and reaction products from them are water-soluble and stable.

In order that chemical reaction is satisfactorily effected for production of carbonic acid gas, it is required that at least one of carbonate or hydrogen carbonate and acidic material is liquid or in solution.

For example, when a solid material having a low water-solubility, such as glutamic acid, is selected as the acidic material calcium carbonate having a low water solubility, chemical reaction is not satisfactorily developed. On the other hand, when liquid acid such as lactic acid and acetic acid, or a solid material having a high water-solubility, such as hydrochloride of glutamic acid and oxalic acid is selected calcium carbonate, chemical reaction is satisfactorily developed to produce a predetermined amount of carbonic acid gas.

According to this invention, there are proposed two methods for producing carbonic acid gas by using the acidic material and at least one kind of carbonate or hydrogen carbonate selected under the above described requirement.

In one method, the acidic material and carbonate or hydrogen carbonate are mixed with each other, or contained separately from each other, inside the hollow fiber permeability apparatus, and they are dissolved into physiological saline solution introduced into the apparatus, to produce carbonic acid gas.

In another method, one of carbonate or hydrogen carbonate and the acidic material is contained in the apparatus, while the other of carbonate or hydrogen carbonate and the acidic material is introduced from the external, or is contained in a circuit connected to the apparatus.

Next, the one method will be described in more details. Equivalent amounts of carbonate or hydrogen carbonate and solid acidic material, are pulverized or granulated, and placed at the inlet portion for the first fluid (for example, blood). Or the pulverized or granulated carbonate or hydrogen carbonate and solid acidic material are enveloped with water-soluble packing material (such as a medicinal wafer), separately and placed at the inlet portion for the first fluid. Preferably, a physiological saline solution is introduced into the inlet portion at the lowest flow rate possible. As soon as the physiological saline solution reaches the chemical compound of carbonate or hydrogen carbonate and acidic material, carbonic acid gas is produced. In that case, it is important to substitute sufficiently air in the inlet portion with the produced carbonic acid gas. Accordingly, it is more preferable that the introduction of the physiological saline solution is ceased for several tens of seconds after several milliliters of physiological saline solution is led into the inlet portion. The produced carbonic acid gas and reaction products are easily dissolved into the physiological saline solution. Accordingly, when the interiors of the hollow fibers are filled with the physiological saline solution, there are no bubbles in the interior of the hollow fibers. This method for removing the gas is very simple, and advantageous in handling of the apparatus.

One of the reaction materials (carbonate or hydrogen carbonate and acidic material) may be previously imparted to the interiors of the hollow fibers, while an excess of the other reaction materials is contained in the inlet portion for the first fluid. In that case, carbonic acid gas is produced also in the interiors of the hollow fibers. Accordingly, the substitution of the gas becomes more sure.

One of the reaction materials can be imparted to the interiors of the hollow fibers in such a manner that it is dissolved, diluted or suspended into a suitable solvent, flowed into the interiors of the hollow fibers and then dried in a suitable manner. Both of the reaction materials may be imparted to the interiors of the hollow fibers from the exterior of the apparatus. In this case, both of the reaction materials are pulverized, then dispersed into a suitable liquid and introduced into the interiors of the hollow fibers.

In the other method, one of the reaction materials, pulverized or granulated, is contained in the inlet portion for the first fluid, while the other of the reaction materials (for example, hydrochloric acid of acetic acid) is introduced into the apparatus from near the inlet portion for the first fluid, by means of a syringe. Also in this method, one of the reaction materials may be imparted to the interiors of the hollow fibers to develop more effective reaction.

Experimentally a necessary volume of carbonic acid gas for obtaining sufficiently the effect of this invention is substantially equal to the priming volume of the first fluid for the apparatus, when one of the reaction materials is imparted to the interior of the hollow fibers. The volume of carbonic acid gas should be substantially twice as much as the priming volume of the first fluid when both of the reaction materials are contained only in the inlet portion of the first fluid. For example, when a normal hollow-fiber permeability apparatus having the blood priming volume of about 100 ml is used, an amount of carbonate or hydrogen carbonate necessary for obtaining carbonic acid gas twice as much as the blood priming volume is about 0.01 mol. It is very little.

Since the chemical compounds used for the production of carbonic acid gas, and the reaction products are water-soluble, they can be very easily removed with physiological saline solution, which is beneficial to the dialysis patient. Sodium hydrogen carbonate, hydrochloride glutamate, L-lactic acid and so on are quite intoxic. Even though they remain in the apparatus, there is no serious problem.

According to this invention, the gas-removing operation, which is very troublesome in the conventional hollow fiber permeability apparatus of the dry type, is much simplified. The conventional hollow-fiber permeability apparatus required about thirty minutes to one hour or more for the gas removing operation.

The method according to this invention is applied not only to the interiors of the hollow fibers, it may be applied also to the exteriors of the hollow fibers. Bubbles existing outside the hollow fibers are apt to adhere to the permeable walls of the hollow fibers, which reduce the effective membrane area of the hollow fibers. Accordingly, the performance of the apparatus can be improved by removing the bubbles from the exteriors of the hollow fibers.

Moreover, this invention is applied not only to the blood dialysis apparatus, but also to an ultrafiltration apparatus and a reverse osmosis apparatus for condensation of juice and purification of water.

Next, this invention will be described in more details with reference to the following Examples.

EXAMPLE 1

First, outline of a blood dialysis apparatus for artificial kidney will be described with reference to FIG. 1.

A permeating region of a housing 1 is occupied with a bundle 3 of hollow fibers 2. The upper and lower end portions of the bundle 3 are fixed with potting materials 4. The upper and lower cut ends of the hollow fibers 2 are communicated with inlet and outlet portions 6 for blood which are defined by covers 5, respectively.

During dialysis, blood 7 is led into the blood inlet portion 6 through a blood inlet tube 8, and uniformly distributed there. The blood 7 flows through the interiors of the hollow fibers 2 into the blood outlet portion 6, and discharged from the apparatus through a blood outlet tube 9.

On the other hand, dialysate 10 is led through an inlet tube 11 into the housing 1, and then flows upwardly through the exteriors of the hollow fibers 2, while waste materials in the blood 7 permeate through the permeable walls of the hollow fibers 7 to move into dialysate 10 flowing through the exteriors of the hollow-fibers 2. Thus, the predetermined dialysis operation is effected. Dialysate 10 is discharged from the housing 1 through an outlet tube 12.

Next, gas removing operation before the blood dialysis will be described.

1 gram of sodium hydrogen carbonate and 2 grams of hydrochloride glutamate are pulverized and mixed, and they are formed into granules. The granules are contained in the blood inlet portion 6. A necessary circuit is connected to the apparatus. The apparatus is upset to put the blood inlet portion 6 now at the lower portion of the housing 1. Then, physiological saline solution is led into the blood inlet portion 6. After a little amount of physiological saline solution is introduced into the blood inlet portion 6, the introduction of the physiological saline solution is temporarily ceased by means of a forceps. The apparatus is left alone for about thirty seconds. Thereafter, physiological saline solution is flowed into the inlet portion at the flow rate of about 100 ml/min for one minute. Thus, the bubble removing operation is performed.

It was visually observed that no bubbles remain in the interiors of the hollow fibers and that no bubbles moves upward from the blood outlet portion. Such a troublesome operation as knocking the apparatus with a forceps, etc. can be omitted. The operating time according to this invention is shorter by more than one hour than the operating time of the conventional method.

For comparison, the bubble-removing operations were performed for ten hollow-fiber permeability apparatus of the same dry type by a skilled workman. The total membrane area and blood priming volume of the apparatus were 1 m² and 100 ml. This operation required at least 32 minutes and up to 93 minutes with a minimum time of 58 minutes.

EXAMPLE 2

0.4 grams of sodium carbonate hydrate was dissolved into 10 ml of glycerine. 40 ml of ethanol was added to the mixture to reduce the viscosity of the mixture. The solution thus prepared was passed through the blood paths of the apparatus. Then, the hollow fibers of the apparatus were dried in the oven at the temperature of 50° C. Thus, sodium carbonate was imparted to the interiors of the hollow fibers. 0.3 grams of pulverized sodium hydrogen carbonate and 1.2 grams of pulverized hydrochloride glutamate were contained in the blood inlet portion 6. The necessary circuit was connected to the apparatus. Then, physiological saline solution was passed through the blood paths at the flow-rate of about 100 ml/min. At the initial stage of the pass-through of the physiological saline solution, some bubbles were observed, since undissolved carbonic acid gas remained in the interiors of the hollow fibers. However, the bubbles soon vanished. The extra bubble-removing operation was not needed.

EXAMPLE 3

0.8 grams of granulated sodium hydrogen carbonate and 1.5 grams of granulated glutamic acid were contained in the blood inlet portion 6 of the apparatus. The same preparation as in the Example 1 was made. The same effect was obtained.

EXAMPLE 4

0.5 grams of lactic acid were dissolved into 100 ml of ethanol. The hollow fibers wee impregnated with the solution, and then dried. 0.8 grams of sodium hydrogen carbonate and 0.4 grams of oxalic acid were contained in the blood inlet portion 6. The bubble-removing test was made. It was confirmed that the extra bubble-removing operation could be omitted, as in the Example 2.

EXAMPLE 5

Figure 2:
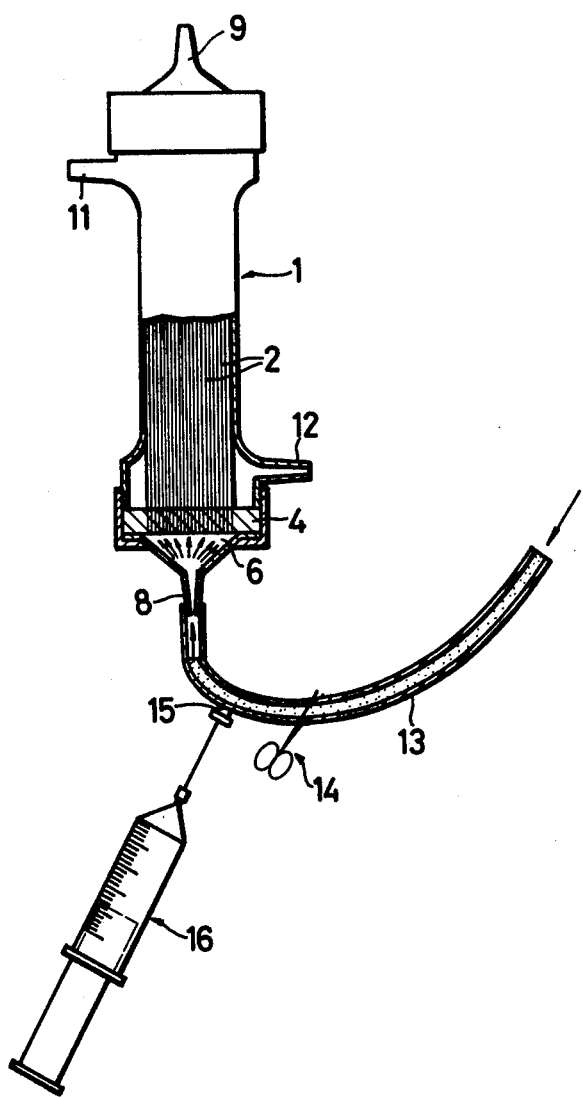
FIG. 2 is a front view illustrating one example of bubble-removing operations according to this invention, partly broken away.

Referring to FIG. 2, 1.5 grams of glutamic acid was contained in the blood inlet portion 6 of the upset apparatus to which the necessary circuit was connected. Physiological saline solution was introduced through a tube 13 directly before the blood inlet portion 6. Then, the introduction of the physiological saline solution was temporarily ceased by a forceps 14. 20 ml of the saturated solution of sodium hydrogen carbonate was injected into the physiological saline solution through an inlet opening 15 made in the tube 13 by a syringe 16. And again physiological saline solution was forced to flow into the blood inlet portion 6. The sodium hydrogen carbonate in the physiological saline solution reacted on the glutamic acid in the blood inlet portion 6 to produce carbonic acid gas. The same gas-removing effect as in the above Examples was obtained.

EXAMPLE 6

Ethanol solution saturated with oxalic acid was sufficiently passed through the blood paths of the apparatus, and then the apparatus was dried. Thus, oxalic acid was imparted to the interiors of the hollow fibers. 0.8 grams of sodium hydrogen carbonate and 0.4 grams of oxalic acid were contained in the blood inlet portion 6. The bubble-removing test was made. It was confirmed that the extra bubble-removing operation could be omitted, as in the Example 2.

EXAMPLE 7

Ethyl alcohol containing 5% by weight of pyruvic acid and 5% by weight of glycerin was passed through the blood paths of the apparatus. The hollow fibers were dried at the room temperature under reduced pressure. Thus, pyruvic acid and glycerin as plasticizer were imparted to the interiors of the hollow fibers. 1 gram of granulated sodium hydrogen carbonate and 0.5 grams of granulated hydrochloride nicotinate were contained in the blood inlet portion 6. The bubble-removing test was made. The same effect as in the above Examples was obtained.

EXAMPLE 8

0.8 grams of granulated sodium hydrogen carbonate was contained in the blood inlet portion 6. 10 ml of 5% dilute hydrochloric acid was added in the same manner as in the Example 5. The same effect as in the Example 5 was obtained. And it was obtained also in the case that 1 ml of acetic acid was used instead of 5% dilute hydrochloric acid.

EXAMPLE 9

1.5 grams of sodium hydrogen carbonate and 0.8 grams of oxalic acid were contained in an enlarged cross-section region 18 defined by an enlarged cross-section portion 17 which was located at the dialysate inlet side of the apparatus. The enlarged cross-section region 18 surrounds the bundle of the hollow fibers. The necessary circuit was connected to the apparatus. The dialysate was flowed at the rate of about 50 ml/min. The amount of the remaining air bubbles outside the hollow-fibers was remarkably reduced in comparison with the conventional dialysis apparatus.

EXAMPLE 10

1.0 gram of granulated sodium hydrogen carbonate 0.8 grams of granulated tartaic acid, and 0.2 grams of granulated hydrochloride glutamate were contained in the blood inlet portion 6 of the apparatus to which the necessary circuit was connected. The apparatus was upset to locate the blood inlet tube 8 at the lower end portion of the housing 1. Physiological saline solution was passed through the blood paths. The same bubble removing effect as in the above Examples was obtained.

While preferred embodiments have been described, variations thereto will occur to those skilled in the art within the scope of the present inventive concepts which are delineated by the following claims.

What is claimed is:

1. A method for removing gas from the interior of a hollow-fiber permeability apparatus in which a permeating region of a housing contains a bundle of hollow fibers, and materials can selectively permeate through the membranes formed by the permeable walls of the hollow fibers, between first and second fluids flowing through said housing inside and outside said fibers respectively, comprising the steps of:

(A), reacting a first material with a second material in at least one part of said apparatus, to produce carbonic acid gas; and (B) substituting the gas previously existing in the interior of said housing with said produced carbonic acid gas.

2. A method according to claim 1, in which said first material is at least one of the inorganic salts selected from a group consisting of metal carbonate, metal sesquicarbonate, ammonium carbonate, ammonium sesquicarbonate, metal hydrogen carbonate, ammonium hydrogen carbonate and mixtures thereof, and said second material is an acidic material, said first material being decomposed with said second material in a short time to produce carbonic acid gas.

3. A method according to claim 2, in which said first material is the selected one from sodium carbonate, sodium hydrogen carbonate, sodium sesquicarbonate, ammonium carbonate, ammonium hydrogen carbonate, calcium carbonate, calcium hydrogen carbonate, magnesium carbonate, calcium magnesium carbonate and mixtures thereof.

4. A method according to claim 2, in which at least one of said first and second materials is liquid or in solution.

5. A method according to claim 2, in which said acidic material is the selected one from inorganic acid, organic compound having at least one of carboxyl group and sulfonic group, inorganic acid salt of organic acid having basic nitrogen and mixtures thereof.

6. A method according to claim 4, in which said inorganic acid is the selected one from hydrochloric acid, sulfuric acid, nitric acid, phosphoric acid, pyrophosphoric acid, tripolyphosphoric acid, sulfurous acid and mixtures thereof.

7. A method according to claim 5, in which said organic compound having at least one of carboxyl group and sulfonic group is the selected one from formic acid, acetic acid, glycolic acid, glyceric acid, lactic acid, pyruvic acid, 2-chloropropionic acid, oxaloacetic acid, citric acid, oxalic acid, tartaric acid, fumaric acid, maleic acid, malonic acid, chlorobenzoic acid, phthalic acid, aconitic acid, salicyclic acid, citramalic acid, gentisic acid, D-glucaric acid, gluconic acid, glutaric acid, gallic acid, L-gluconic acid, hydroxyphthalic acid, galacturonic acid, lactobionic acid, n-nitro-4-sulfobenzoic acid, P-toluenesulfonic acid, benzene sulfonic acid, 4-hydroxyisophthalic acid and mixtures thereof.

8. A method according to claim 5, in which said amino acid is the selected one from glutamic acid and hydroxyglutamic acid.

9. A method according to claim 4, in which said inorganic acid salt of organic acid having basic nitrogen is the selected one from the hydrochloride salt of, sulfate of, or phosphate of aminosalicylate, cinchomeronate, cinchophene, indican, indoleacetate, isonicotinate, isonipecotate, nicotinate, pipecolate, proline, and mixtures thereof.

10. A method according to claim 4 in which said organic acid is amino acid.

11. A method according to claim 1, in which said first and second materials are mixed with each other, or separated from each other, in said hollow fiber permeability apparatus, and are dissolved into water or physiological saline solution which is introduced into said hollow fiber permeability apparatus, to react with each other.

12. A method according to claim 11, in which said first and second materials are solid, and pulverized or granulated, being contained in the inlet portion for said first fluid in said hollow fiber permeability apparatus.

13. A method according to claim 11, in which the first reaction component selected from said first and second materials is contained in the exteriors of said hollow fibers, while the other reaction component to react with said first reaction component is contained in the inlet portion for said second fluid in said hollow fiber permeability apparatus, whereby carbonic acid gas is produced in the exteriors of said hollow fibers.

14. A method according to claim 12, in which said first and second materials are enveloped with water-soluble packing materials, respectively.

15. A method according to claim 11, in which the first reaction component selected from said first and second materials is contained in the interiors of said hollow fibers, while the other reaction component to react with said first reaction component is contained in the inlet portion for said first fluid in said hollow fiber permeability apparatus, whereby carbonic acid gas is produced in the interiors of said hollow fibers.

16. A method according to claim 11, in which the first reaction component selected from said first and second materials is contained in the interiors of said hollow fibers, while said first reaction component and an excess of the other reaction component to react with said reaction component are contained in the inlet portion for said first fluid in said hollow fiber permeability apparatus, whereby carbonic acid gas is produced both in the inlet portion for said first fluid and in the interiors of said hollow fibers.

17. A method according to claim 11, in which said first and second materials are pulverized and dispersed into a liquid, said liquid being introduced into the interiors of said hollow fibers.

18. A method according to claim 11, in which the first reaction component selected from said first and second materials is contained in the exteriors of said hollow fibers, while said first reaction component and an excess of the other reaction component to react with said first reaction component are contained in the inlet portion for said second fluid in said hollow fiber permeability apparatus, whereby carbonic acid gas is produced both in the inlet portion for said second fluid and in the exteriors of said hollow fibers;

19. A method according to claim 11, in which said first and second materials are pulverized and dispersed into a liquid, said liquid being introduced into the exteriors of said hollow fibers.

20. A method according to claim 1, in which the first reaction component selected from said first and second materials is contained in said hollow fiber permeability apparatus, while the other reaction component to react with said first reaction component is introduced from the exterior of said hollow fiber apparatus, or contained in a circuit connected to said hollow fiber permeability apparatus.

21. A method according to claim 20, in which said first reaction component is pulverized or granulated, and contained in the inlet portion for said first fluid, while said other reaction component is introduced from near said inlet portion for said first fluid.

22. A method according to claim 20, in which said first reaction component is dissolved, diluted or suspended into a solvent, introduced into the interiors of said hollow fibers, and dried there to be placed or added to the interiors of said hollow fibers.

23. A method according to claim 11, in which said first reaction component is pulverized or granulated, and contained in the inlet portion for said second fluid, while said other reaction component is introduced from near said inlet portion for said second fluid.

24. A method according to claim 11, in which said first reaction component is dissolved, diluted or suspended into a solvent, introduced into the exteriors of said hollow fibers, and dried there to be imparted to the exteriors of said hollow fibers.

25. A method according to claim 11, in which said first and second materials are solid, and pulverized or granulated, being contained in the inlet portion for second fluid in said hollow fiber permeability apparatus.

26. A method according to claim 25, in which said first and second materials are enveloped with water-soluble packing materials, respectively.

27. In a hollow-fiber permeability apparatus in which a permeating region of a housing contains a bundle of hollow fibers being fixed thereto by a potting material, and wherein materials can selectively permeate through the membranes formed by the permeable walls of the hollow fibers, between first and second fluids flowing through said housing inside and outside said fibers respectively, the improvements in which at least one of first and second materials to produce carbonic acid gas by mutual chemical reaction is contained in an inlet portion for said first fluid, said inlet portion being defined by said potting material and by a cover disposed over potting material, and a tube connected to said cover and communicating with said inlet portion for introducing a saline solution into said inlet portion.

28. An apparatus according to claim 27, in which said first material is at least one of the inorganic salts selected from a group consisting of metal carbonate, metal sesquicarbonate, ammonium carbonate, ammonium sesquicarbonate, metal hydrogen carbonate, ammonium hydrogen carbonate and mixtures thereof, and said second material is an acidic material, said first material being decomposed with said second material in a short time to produce carbonic acid gas.

29. An apparatus according to claim 28, in which said first material is the selected one from sodium carbonate, sodium hydrogen carbonate, sodium sesquicarbonate, ammonium carbonate, ammonium hydrogen carbonate, calcium carbonate, calcium hydrogen carbonate, magnesium carbonate, calcium magnesium carbonate and mixtures thereof.

30. An apparatus according to claim 28, in which said acidic material is the selected one from inorganic acid, organic compound having at least one of carboxyl group and sulfonic group, inorganic acid salt or amino acid, inorganic acid salt of organic acid having basic nitrogen and mixtures thereof.

31. An apparatus according to claim 30, in which said organic compound having at least one of carboxyl group and sulfonic group is the selected one from formic acid, acetic acid, glycolic acid, glyceric acid, lactic acid, pyruvic acid, 2-chloropropionic acid, oxaloacetic acid, citric acid, oxalic acid, tartaric acid, fumaric acid, maleic acid, malonic acid, chlorobenzoic acid, phthalic acid, aconitic acid, salicylic acid, citramalic acid, gentisic acid, D-glucaric acid, gluconic acid, glutaric acid, gallic acid, L-gluconid acid, hydroxyphthalic acid, galacturonic acid, lactobionic acid, 2-nitro-4-sulfobenzoic acid, P-toluenesulfonic acid, benzene sulfonic acid, 4-hydroxyisophthalic acid, and mixtures thereof.

32. An apparatus according to claim 30, in which said amino acid is the selected one from glutamic acid, and hydroxyglutamic acid.

33. An apparatus according to claim 30, in which said inorganic acid salt of organic acid having basic nitrogen is the selected one from hydrochloride salt of, sulfate of, or phosphate of aminosalcylate, cinchomeronate, cinchophene, indican, indoleacetate, isonicotinate, isonipecotate, nicotinate, pipecolate, proline, and mixtures thereof.

34. An apparatus according to claim 30 in which said organic acid is amino acid.

35. An apparatus according to claim 30, in which said inorganic acid is the selected one from hydrochloric acid, sulfuric acid, nitric acid, phosphoric acid, pyrophosphoric acid, sulfurous acid and mixtures thereof.

36. An apparatus according to claim 27, in which at least one of said first and second materials is liquid or in solution.

37. An apparatus according to claim 27, in which said first and second materials are mixed with each other, or separated from each other, in said hollow fiber permeability apparatus, and are dissolved into water or physiological saline solution which is introduced into said hollow fiber permeability apparatus, to reset with each other.

38. An apparatus according to claim 37, in which said first and second materials are solid, and pulverized or granulated, being contained in the inlet portion for said first fluid in said hollow fiber permeability apparatus.

39. An apparatus according to claim 38, in which said first and second materials are enveloped with water-soluble packing materials, respectively.

40. An apparatus according to claim 37, in which the first reaction component selected from said first and second materials is contained in the interiors of said hollow fibers, while the other reaction component to react with said first reaction component is contained in the inlet portion for said first fluid in said hollow fiber permeability apparatus, whereby a carbonic acid gas is produced in the interiors of said hollow fibers.

41. An apparatus according to claim 37, in which the first reaction component selected from said first and second materials is contained in the interiors of said hollow fibers, while said first reaction component and an excess of the other reaction component to react with said first reaction component are contained in the inlet portion for said first fluid in said hollow fiber permeability apparatus, whereby carbonic acid gas is produced both in the inlet portion for said first fluid and in the interiors of said hollow fibers.

42. An apparatus according to claim 37, in which said first and second materials are pulverized and dispersed into a liquid, said liquid being introduced into the interiors of said hollow fibers.

43. An apparatus according to claim 37, in which said first and second materials are solid, and pulverized or granulated, being contained in the inlet portion for second fluid in said hollow fiber permeability apparatus.

44. An apparatus according to claim 38, in which said first and second materials are enveloped with water-soluble packing materials, respectively.

45. An apparatus according to claim 37, in which one of said first and second materials is contained in the exteriors of said hollow fibers, while the other of said first and second materials is contained in the inlet portion for said second fluid in said hollow fiber permeability apparatus whereby carbonic acid gas is produced in the exteriors of said hollow fibers.

46. An apparatus according to claim 37 in which one of said first and second materials is contained in the exteriors of said hollow fibers, while the one of said first and second materials, and an excess of the other of said first and second materials are contained in the inlet portion for said second fluid in said hollow fiber permeability apparatus, whereby carbonic acid gas is produced both in the inlet portion for said second fluid and in the exteriors of said hollow fibers.

47. An apparatus according to claim 37, in which said first and second materials are pulverized and dispersed into a liquid, said liquid being introduced into the exteriors of said hollow fibers.

48. An apparatus according to claim 27, in which the first reaction component selected from said first and second materials is contained in said hollow fiber permeability apparatus, while the other reaction component to react with said first reaction component is introduced from the exterior of said hollow fiber apparatus, or contained in a circuit connected to said hollow fiber permeability apparatus.

49. An apparatus according to claim 48, in which said first reaction component is pulverized or granulated, and contained in the inlet portion for said first fluid, while said other reaction component is introduced from near said inlet portion for said first fluid.

50. An apparatus according to claim 48, in which said first reaction component is disposed in a solvent which has been introduced into the interiors of said hollow fibers, and dried whereby said component becomes associated with the interiors of said hollow fibers.

51. An apparatus according to claim 48 in which one of said first and second materials is pulverized or granulated, and contained in the inlet portion for said second fluid, while the other of said first and second materials is introduced from near said inlet portion for said second fluid.

52. An apparatus according to claim 48, in which said one of first and second materials is dissolved, diluted or suspended into a solvent, introduced into the exteriors of said hollow fibers, and dried there to be imparted to the exteriors of said hollow-fibers.

53. An apparatus according to claim 27 comprising a blood dialyzer.

54. An apparatus according to claim 27 comprising a hollow fiber ultrafiltration apparatus.

55. An apparatus according to claim 27 comprising a reverse osmosis apparatus.

* * * * *